ized Patent [19]

United States Patent [19]

Borden et al.

[11] Patent Number: 4,804,853
[45] Date of Patent: Feb. 14, 1989

[54] COMPACT PARTICLE FLUX MONITOR

[75] Inventors: Peter Borden, Palo Alto; Laszlo Szalai, Mt. View; Jon Munson, Sunnyvale, all of Calif.

[73] Assignee: High Yield Technology, Mountain View, Calif.

[21] Appl. No.: 41,795

[22] Filed: Apr. 23, 1987

[51] Int. Cl.⁴ .............................. G01H 15/06
[52] U.S. Cl. ................... 250/574; 356/338; 356/343
[58] Field of Search ............... 250/573, 574, 564–565; 356/338–343

[56] References Cited

U.S. PATENT DOCUMENTS

| | | | |
|---|---|---|---|
| 4,420,256 | 12/1983 | Fladda et al. | 356/343 |
| 4,571,079 | 2/1986 | Knollenberg | 356/339 |
| 4,573,796 | 3/1986 | Martin et al. | 357/343 |
| 4,591,268 | 5/1986 | Lew | 356/338 |

Primary Examiner—Edward P. Westin
Assistant Examiner—Khaled Shami
Attorney, Agent, or Firm—Nathan N. Kallman; Alan H. MacPherson; Paul J. Winters

[57] ABSTRACT

A compact particle flux monitor is formed with an enclosure through which a laser beam is directed by a lens. An aperture in the enclosure allows free particles which are to be detected to pass through a sensing area at a limiting acceptance angle thereby providing an indication of direction of particle flow. Photodiodes mounted at the sensing area detect the particles, including relatively small particles, by means of the high intensity beam portion at the region of the focal point of the light beam. The response region along the diverging beam is relatively long so that the response as a function of particle size is above background noise level.

16 Claims, 5 Drawing Sheets

4,804,853

COMPACT PARTICLE FLUX MONITOR

REFERENCE TO COPENDING APPLICATION

Copending U.S. patent application Ser. No. 06/907,776, filed Sept. 16, 1986, now U.S. Pat. No. 4,739,177, a particle detector for wafer processing equipment wherein particles are sensed by means that detect light scattered by the particles.

FIELD OF THE INVENTION

This invention relates to a compact particle flux monitor used for detecting contaminant particles in vacuum equipment.

BACKGROUND OF THE INVENTION

During the production of integrated circuits, semiconductor devices, magnetic disks, optical disks and the like, free contaminant particles are usually present in the processing equipment and in the environment in which the constituents being processed are disposed. The contaminant particles that are found, particularly in the gases and liquids employed in the processing equipment, adversely affect the circuits, devices and assemblies being produced Therefore it has been found necessary to detect or sense the number and density of particles so that the process operator can determine whether the magnitude of contamination is greater than a predetermined threshold of particle density.

To accomplish the desired detection, sensor technology that monitors the flow or flux of particles in free space is utilized. The requirements of a sensor for monitoring particles are that it can operate in a vacuum, that it is compact enough to fit into existing equipment, that it does not contaminate the vacuum, and that it provides real-time data. Also, if possible the sensor should be able to tolerate the harsh environments, which may contain free fluorine or chlorine radicals, for example, that may be present in the processing equipment. In addition, because the gas flows that are formed in and around such processing equipment are frequently turbulent and carry small particles, it is desirable to be able to sense the direction of motion of the particles.

When operating with detection instruments that determine the number of free particles in gases and liquids, it is assumed that the particulate is suspended in the gas or liquid. The gas or liquid acts as a carrier to transport the suspended particles through the focus of a laser beam that is used with the detection equipment. The suspended particles scatter light that enables detection and thereby provide an indication of the size of the particles.

However, the sensor technology that has been employed is characterized by severe limitations when used in vacuum equipment. For example, it is not feasible to employ a gas as a carrier that will bring the particles to the focus point of a laser beam. Also, a measurement technique using a carrier gas is not passive because the carrier gas is drawn from the measurement point. Therefore, the gas flow is affected and environmental conditions at the point of measurement are affected, particularly when measurements are done in small volume vessels. Since there is a time delay between the time the gas enters the tube which is used to draw the carrier gas to the laser, and the time when the gas passes the laser beam, it is apparent that such a measurement does not occur in real time. The results obtained with such equipment are difficult to correlate to actual events at the point of measurement. Furthermore, the carrier gas measurement relies on the assumption that the particles remain in suspension. But it is known that heavier particles are not suspended to enable proper measurement and therefore the heavier particles will not be detected. In addition, such measurements provide no information about the direction of particle motion, since the drawing of carrier gas is an isotropic process.

It would be highly advantageous to provide a particle detection apparatus wherein a high intensity response to detected particles, including small particles, is obtained, and wherein the area of the response region, over which the response as a function of particle size is above the background noise level, is significantly extended.

SUMMARY OF THE INVENTION

An object of this invention is to provide a particle flux monitor that realizes a high intensity response during detection of free particles in gases or liquids.

Another object of this invention is to provide a compact particle flux monitor wherein the area of the effective response region is substantially increased.

According to this invention, a compact particle flux monitor comprises a source of a high intensity light beam, photocell means for sensing light that is scattered by particles on which the beam impinges, and a sensing area with an aperture that defines a limitation of the acceptance angle of the path of particles that intercept the beam, thereby providing a directionality aspect to particle travel, which can be determined by calculation. An optimal focal spot of the light beam is established so that at the region where the beam converges and has a high intensity per unit area, the level of response to detected particles is increased. In addition, the length over which a significant response is received is extended.

DESCRIPTION OF THE DRAWINGS

The invention will be described in detail with reference to the drawings in which.

Similar numerals refer to similar elements throughout the drawing.

DETAILED DESCRIPTION OF THE INVENTION

Figure 1:
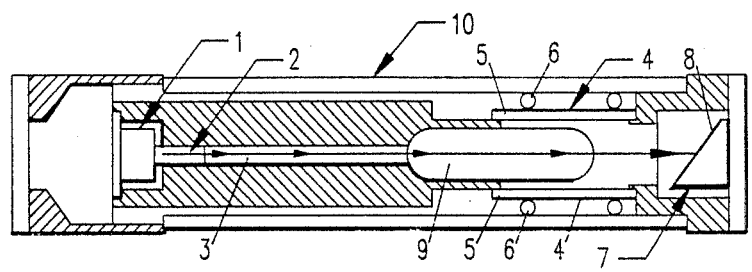
FIG. 1 is a top sectional view of a compact particle flux monitor, made in accordance with this invention.
Figure 2:
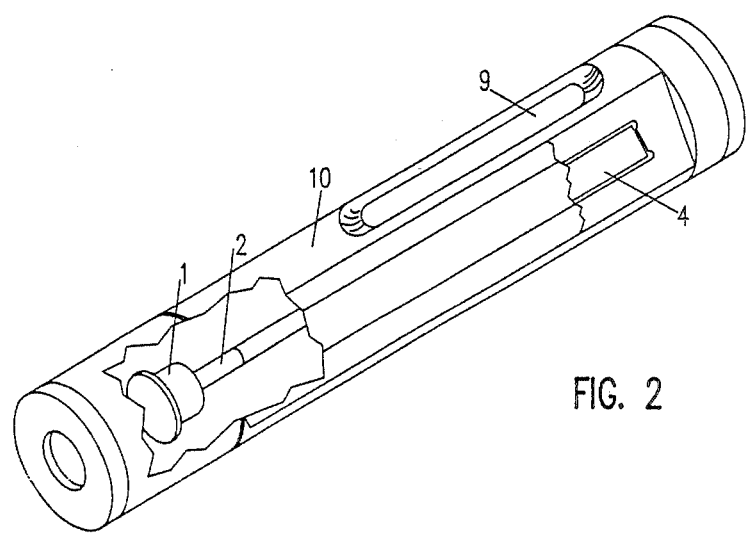
FIG. 2 is an isometric view, partly broken away, of the flux monitor of FIG. 1.

In an embodiment of this invention as depicted in FIGS. 1 and 2, a particle flux monitor is formed with an enclosure 10, preferably made of aluminum or stainless steel. The enclosure houses a laser diode 1 that provides a short wavelength light beam of about 780 nanometers for example. The laser diode may be an AlGaAs laser having an output power of approximately 20 milliwatts by way of example. The laser diode structure is relatively compact and low in cost. The compact size of the laser diode allows the sensor assembly to be retrofitted into existing conventional equipment without modification to the equipment or the sensor. The low cost of the particle flux monitor allows the use of multiple sensors without imposing prohibitive cost. The use of a short wavelength laser allows the detection of relatively small particles.

In operation, the laser beam 3 passes through a focusing lens 2, which may be a gradient index rod lens having a pitch of 0.11 as an example. The light beam passes through a sensing area adjacent to an aperture 9 and strikes a beam stop 7. The surface of the beam stop is coated with a material 8 which may be a piece of silicon having an antireflection coating that absorbs light and reflects the remainder into the beam stop cavity, so that back scatter of laser light into the sensing area is prevented. The sensing area is defined by the geometry of the aperture, which is depicted as elliptical in shape in this implementation.

The scattered light which is developed by the impact of the beam on particles that pass through the sensing area is collected by means of silicon photodiodes 4 which are assembled about 180° apart on both sides of the light beam 3. The photodiodes, which may be 0.5 cm×2.5 cms in size, are maintained in place with rubber mounts 6 and are covered with filters 5, made of Schott RG9 glass by way of example. The filters have a peak transmission at the laser wavelength of 780 nm so that they effectively filter out excess stray light. The distance from the beam path orthogonally to each photocell 4 is approximately 0.5 cm for this embodiment.

During the operation of the particle flux monitor, particles in a gas or liquid flow pass through the aperture 9 and a portion of these particles move through the laser beam 3. The particles that traverse the beam cause light scattering and part of the scattered light lands on the photocells 4 which generate an electrical signal representative of the light received. The amplitude of the signal is an approximate indication of particle size. The generated electrical signals are filtered to eliminate DC response, thereby allowing the sensor to detect only moving particles and to be relatively insensitive to stray light.

Figure 6:
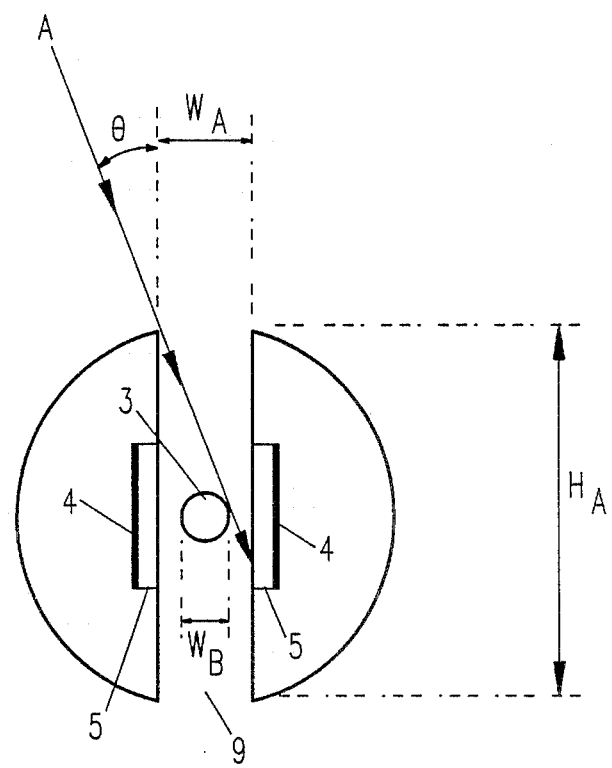
FIG. 6 is a representational end view of a particle flux monitor indicating the limitation on the acceptance angle relative to the beam path imposed by the aperture located in the novel structure.

In accordance with one feature of this invention, the aperture 9 of the sensing area is shaped to allow particles to fall or pass through to the sensing area and to provide a directional capability to the sensor assembly, as illustrated in the end view of FIG. 6. The directional capability is dependent upon the acceptance angle $\phi$ which is defined by the relation $$\phi = \tan^{-1}\left(\frac{W_A}{H_A}\right) + \tan^{-1}\left(\frac{W_B}{\sqrt{H_A^2 + W_A^2}}\right),$$

where $\phi$ is the acceptance angle for the extreme path A that a particle can travel through the aperture and still intercept the beam; $H_A$ and $W_A$ are the height and width respectively of the sensing area defined by the aperture 9 and $W_B$ is the diameter of the beam.

Figure 3:
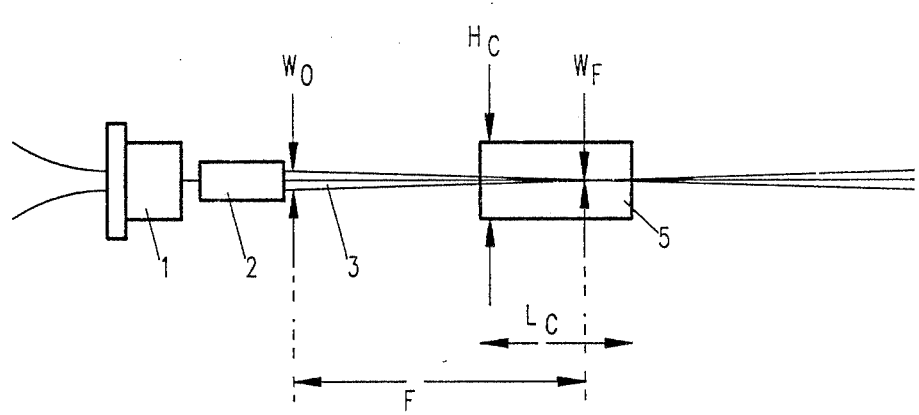
FIG. 3 is a representational view of a light beam and photocell arrangement to aid in the explanation of the invention.

Another feature of the particle flux monitor of this invention is the placement of the focal spot of the laser beam at an optimal point. As shown in FIG. 3, the beam 3 emerges from the lens 2 with a diameter $W_0$. The beam attains a minimum diameter $W_F$ at the focal point at a focal length F and then diverges as it progresses through the sensor assembly. The focal length is the distance from the lens 2 to the focal point F, and is measured from the end of the lens facing the photocells. The beam has a diameter of about 1 mm at the lens and converges to an approximate diameter of 0.1 mm at the focal point in this embodiment.

Figure 4:
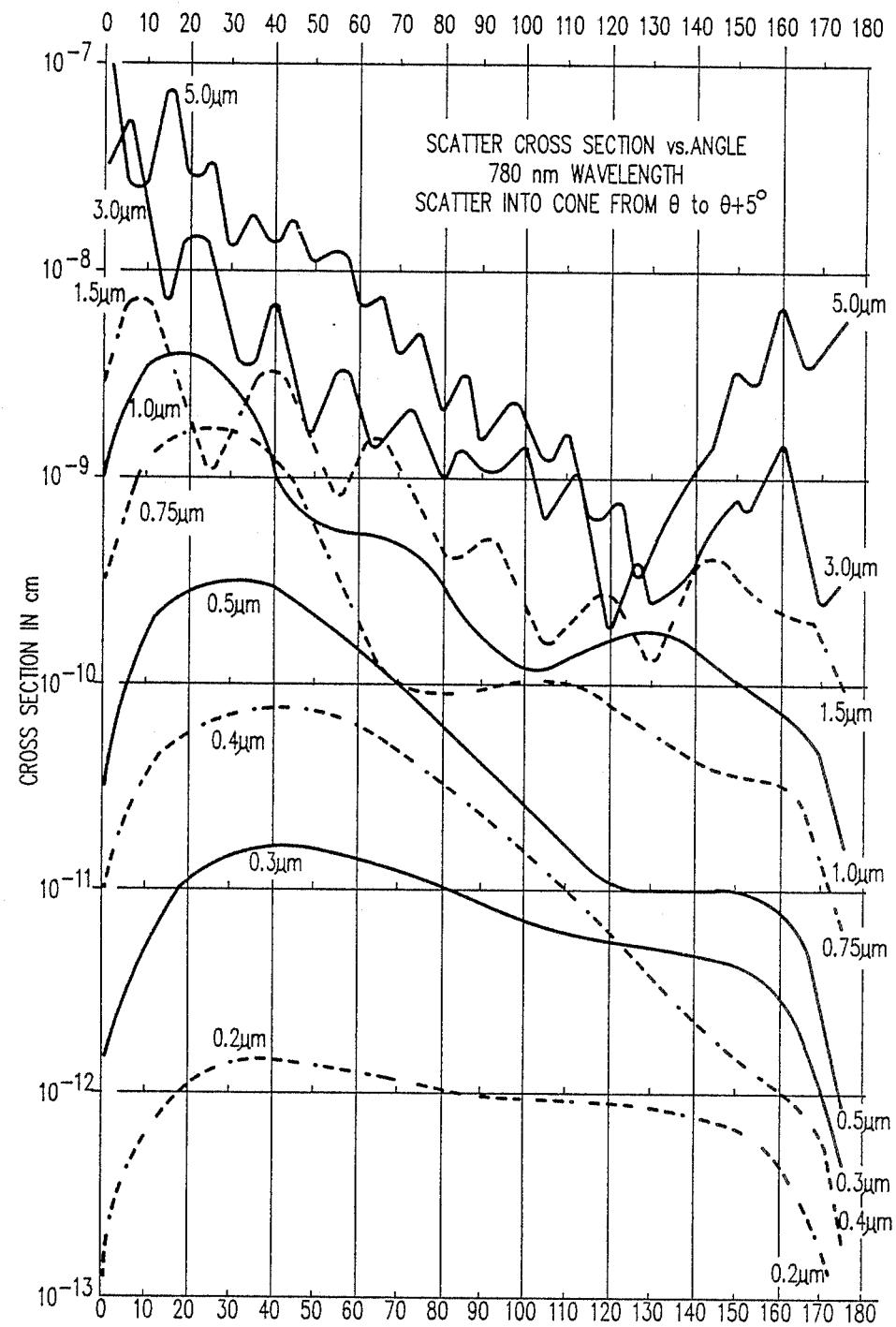
FIG. 4 is a series of curves plotting the scattering cross-section of the particle flux monitor measured in micrometers, as a function of the scatter angle $\theta$.

It is known that light that scatters from small particles tends to be stronger in the forward direction than in the backward direction. As shown in FIG. 4, which is a plot of the scattering cross-section in centimeters as a function of angle $\theta$ at 780 nm wavelength for various sizes of spherical particles with an index of refraction of 1.5, the forward scattering or scattering at angles less than 90° is stronger than the backward light scattering. The angle $\theta$ is the angle of distribution of the scattered light relative to the axial path of the beam.

Three factors need to be considered to determine the optimum location for the focal spot of the beam. First, signals from scattered light are stronger if the detector is located so that it collects forward scatter. Secondly, signals from scattered light are stronger if the detector photodiodes view the focal spot. And third, the area of the beam and thus the probability of a particle passing through the beam increases as the distance from the focal spot increases.

Figure 5:
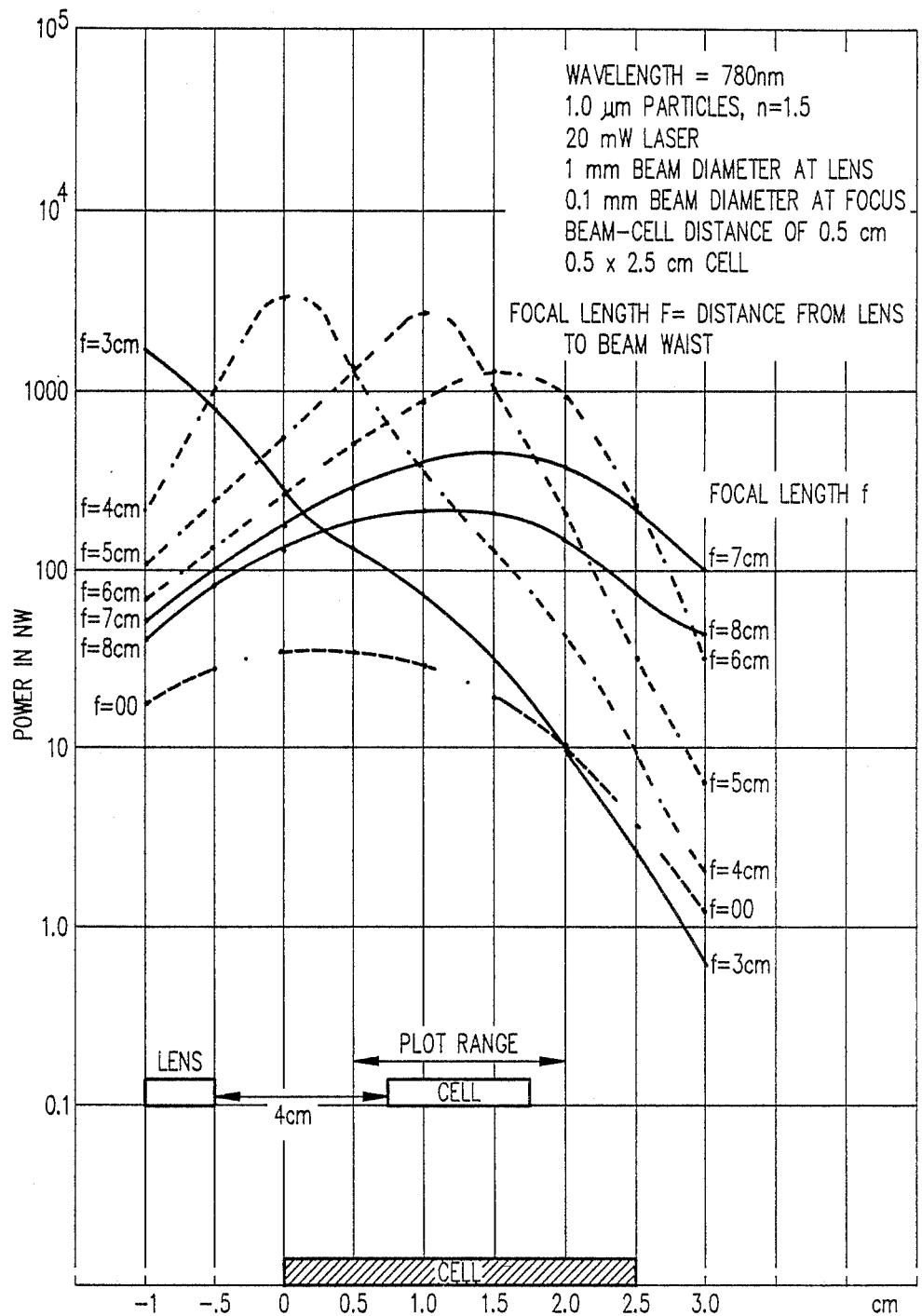
FIG. 5 is a series of curves plotting power in nanowatts collected by a single photocell as a function of distance in centimeters relative to points along the beam axis.

With reference to FIG. 5, these three factors are balanced so that the response to the scattered light will increase while maintaining a high probability that a particle will pass through the beam. FIG. 5 illustrates the power of the signal that is collected by a single photocell as a function of the position of the particle that passes through the beam axis for various locations of the focal point. The distance between the lens and the ends of the photocells facing the lens, which are in radial alignment in this implementation, is preferably held constant at about 4 cm.

For example, when the focal point is beyond the other ends of the photocells furthest from the lens, as in the example where the focal length F=7 cm, the beam converges so that its intensity per unit area is increasing, while the ratio of back to forward scatter collected by the photocells increases. The result is a relatively flat response with an intensity well above that of the F=∞ example, and the length of the response region is over 4 cm. In the example where F=4 cm, wherein the focal point is in alignment with the ends of the photocells facing the lens, the response is further increased while maintaining the benefit of the beam convergence to counteract the decreasing intensity as the back to forward scatter ratio increases. With the focal length F=4 cm, a very high response and a relatively long response region are realized.

In contrast, an extreme case exists if the beam is unfocused, as occurs when the focal length F is infinity. In such case the response is low and, if the noise level is 20 nanowatts, the response length is about 2.4 cm, by way of example. In another extreme situation, when the focal length is 3 cm and the focal point is in the area between the lens and the ends of the cells facing the lens, the beam is diverging as it passes through the cells, and the ratio of back to forward scatter is also increasing. As a result the response drops off rapidly. The response length in this case is about 2.6 cm and the amplitude of the response is above that for the F=∞ case for most of this length, and as the beam has a smaller size, it is less likely that a particle will intercept it.

Thus, in an implementation where the focal length F=3, wherein the focal point is approximately 1 cm from the end of the photocell facing the lens in the direction towards the lens, the response level is decreased significantly when compared to a focal length F which is in the range of 4-8 cm, for example. Similarly, if a focal length of 9 cm is used so that the focal point is approximately 5 cm from the end of the photocell that faces the lens in a direction away from the lens towards the other end of the photocell, the intensity of response is lowered, because there is not enough convergence of the beam. Therefore, a desirable range is restricted to focal lengths in a range between 3-9 cm, when the lens and photocells are spaced 4 cm apart, as measured axially along the beam path.

In an alternative embodiment the filters 5 covering respective photocells 4 are coated with a protective material such as sapphire or silicon nitride to protect the photocells against erosion by corrosive atmospheres, such as found with plasma etchers. A window that is coated with the same material is placed at the point where the beam 3 enters the sensing area 9, and the beam stop reflector is also coated with sapphire or silicon nitride.

It should be understood that the invention disclosed herein is not limited to the particular parameters, dimensions or materials specified above. For example, the focal length may be selected to be other than 4 cm, and the cells size may be varied. The number of cells may be other than two, and the cells need not be in radial alignment. The aperture for determining directionality can be shaped differentially than elliptical. Other modification may be made within the scope of this invention.

By virtue of the design of the particle flux monitor disclosed herein, a very high intensity signal is obtained thereby enabling detection of very small particles, in the order of 0.5 μm. In addition, the usable beam area for detection is substantially extended since a response is obtained above the background noise over as much of the beam as possible. The usable beam area is very small near the focus where the intensity, and thus the scattered intensity is very large. The usable beam area increases away from the focus such that the intensity of the signal becomes smaller. The detection monitor design disclosed herein effectively balances the effects of beam convergence and the varying ratio of back to forward scatter collection.

What is claimed is:

1. A compact particle flux monitor for detecting particles in a vacuum or low pressure environment comprising:
    an enclosure having a longitudinal axis;
    a source for providing a high intensity light beam along a longitudinal path having a focal point within said enclosure;
    at least one aperture formed in said enclosure for allowing passage of particles into said enclosure so that said particles traverse said light beam, said aperture extending in a direction substantially parallel to said beam path;
    photosensor means assembled to said enclosure for sensing light scattered by said particles as they pass through said light beam, said photosensor means extending longitudinally in a direction parallel to said beam path, said photosensor means being positioned so that sensing portions of said photosensor means are located radially relative to said focal point of said beam path.

2. A monitor as in claim 1 wherein said enclosure is cylindrical or rectangular.

3. A monitor as in claim 1 wherein said light beam source is a laser diode.

4. A monitor as in claim 1 wherein said light beam source is an aluminum gallium arsenic laser diode.

5. A light beam as in claim 4 wherein said laser diode operates at a wavelength of approximately 780 nanometers.

6. A monitor as in claim 1 including a lens that is a gradient index rod lens for focusing said beam.

7. A monitor as in claim 6 wherein said lens has a pitch of about 0.11.

8. A monitor as in claim 1 wherein said focal point is approximately between 3-9 centimeters from said lens.

9. A monitor as in claim 8 wherein said laser beam has a diameter of 1 millimeter emanating from said lens and a diameter of 0.1 millimeter at said focal point.

10. A monitor as in claim 6 including a beam stop at the end of the axial path of the light beam.

11. A monitor as in claim 10 including a coating on said beam stop to prevent backscatter of light to said sensing area.

12. A monitor as in claim 8 wherein said photosensor means comprise a pair of photodiodes mounted to said enclosure that are spaced approximately 180° apart, each photodiode having an end facing the end of said lens from which the beam emanates.

13. A monitor as in claim 12 wherein said focal point is established at the ends of said photodiodes which face said lens.

14. A monitor as in claim 12 wherein the focal point is formed on said axial path at a distance within a range defined at one extreme by the distance of about Lc/3 from said end of said photodiode facing the end of said lens in a direction towards said lens, and at the other extreme at a distance of about Lc from said end of said photodiode in a direction away from said lens, wherein Lc is the length of said photodiode.

15. A monitor as in claim 12 wherein said photodiode means comprise glass filters to filter out excess stray light.

16. A monitor as in claim 12 wherein the flow of particles that passes through said aperture is limited by an acceptance angle defined by $$\phi = \tan^{-1}\left(\frac{W_A}{H_A}\right) + \tan^{-1}\left(\frac{W_B}{\sqrt{H_A^2 + W_A^2}}\right),$$

wherein $W_A$ is the width and $H_A$ is the height respectively of said sensing area, and $W_B$ is the diameter of said light beam.

* * * * *